(12) United States Patent
Cinader, Jr. et al.

(10) Patent No.: US 7,168,950 B2
(45) Date of Patent: Jan. 30, 2007

(54) ORTHODONTIC METHODS AND APPARATUS FOR APPLYING A COMPOSITION TO A PATIENT'S TEETH

(75) Inventors: David K. Cinader, Jr., Yorba Linda, CA (US); Russell A. Jordan, Rancho Cucamonga, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 121 days.

(21) Appl. No.: 10/967,797

(22) Filed: Oct. 18, 2004

(65) Prior Publication Data

US 2006/0084026 A1    Apr. 20, 2006

(51) Int. Cl.
*A61C 7/00*      (2006.01)
*A61C 5/00*      (2006.01)

(52) U.S. Cl. .............................. 433/2; 433/24; 433/80
(58) Field of Classification Search ................ 433/2, 433/6, 24, 80
See application file for complete search history.

(56) References Cited

U.S. PATENT DOCUMENTS

| | | | |
|---|---|---|---|
| 4,290,174 A | | 9/1981 | Kalleberg |
| 4,526,540 A | * | 7/1985 | Dellinger ................. 433/24 |
| 4,984,339 A | | 1/1991 | Provost et al. |
| 5,152,917 A | | 10/1992 | Pieper et al. |
| 5,165,424 A | * | 11/1992 | Silverman ................ 128/861 |
| 5,354,199 A | | 10/1994 | Jacobs et al. |
| 5,500,273 A | | 3/1996 | Holmes et al. |
| 5,538,129 A | | 7/1996 | Chester et al. |
| 5,707,235 A | | 1/1998 | Knutson |
| 5,971,754 A | | 10/1999 | Sondhi et al. |
| 6,050,815 A | | 4/2000 | Adam et al. |
| 6,123,544 A | | 9/2000 | Cleary |
| 6,126,443 A | | 10/2000 | Burgio |
| 6,142,780 A | | 11/2000 | Burgio |
| 6,322,360 B1 | | 11/2001 | Burgio |
| 6,528,555 B1 | | 3/2003 | Nikutowski |
| 6,607,382 B1 | | 8/2003 | Kuo et al. |
| 6,705,863 B2 | | 3/2004 | Phan et al. |
| 2003/0194677 A1 | | 10/2003 | Sachdeva et al. |
| 2003/0196914 A1 | | 10/2003 | Tzou et al. |
| 2004/0166462 A1 | | 8/2004 | Phan et al. |
| 2004/0219471 A1 | | 11/2004 | Cleary et al. |

FOREIGN PATENT DOCUMENTS

| | | |
|---|---|---|
| WO | WO 94/23610 | 10/1994 |
| WO | WO 98/30381 | 7/1998 |
| WO | WO 98/57564 | 12/1998 |

OTHER PUBLICATIONS

Pending U.S. Appl. No. 10/678,286, filed Oct. 3, 2003 (58655US002).
Pending U.S. Appl. No. 10/742,561, filed Dec. 19, 2003 (59428US002).

* cited by examiner

*Primary Examiner*—Cary E. O'Connor
(74) *Attorney, Agent, or Firm*—James D. Christoff (57) ABSTRACT

Transfer apparatus is constructed for applying an orthodontic composition such as a bonding composition to selected areas of multiple teeth simultaneously. The selected areas of the teeth that receive the composition substantially correspond to areas of the teeth that subsequently receive orthodontic appliances. As a result, contact of the composition with other regions of the oral cavity such as the gingival tissue is avoided.

34 Claims, 4 Drawing Sheets

ORTHODONTIC METHODS AND APPARATUS FOR APPLYING A COMPOSITION TO A PATIENT'S TEETH

BACKGROUND OF THE INVENTION

1. Field of the Invention

This invention relates to methods and apparatus used in an orthodontic treatment program to apply a composition to external areas of the patient's teeth.

2. Description of the Related Art

Orthodontic treatment involves movement of malpositioned teeth to improved locations. Orthodontic treatment can greatly enhance the aesthetic appearance of the patient, especially in areas near the front of the oral cavity. Orthodontic treatment can also improve the patient's occlusion so that the teeth function better with each other during mastication.

One type of common orthodontic treatment program includes the use of a set of small slotted appliances known as brackets. The brackets are affixed to the patient's teeth and an archwire is placed in the slot of each bracket. The archwire forms a track to guide movement of the teeth to desired positions. End portions of the archwire are often captured in buccal tube appliances that are affixed to the patient's molar teeth.

Many orthodontic appliances are directly bonded to the patient's tooth enamel by an adhesive composition. The adhesive composition may be a photocurable adhesive, which begins to cure upon exposure to light in certain ranges of wavelength. Another common type of orthodontic bonding composition is provided as two initially separate components that begin to cure once mixed together.

Regardless of the type of bonding composition used by the practitioner, it is important that bond failures do not occur and that the appliances remain securely fixed to the teeth for the intended length of treatment time. If, for example, one or more of the appliances detach from the teeth during the course of treatment, the progress of treatment is often interrupted and the patent should then return to the practitioner's office for reattachment or replacement of the detached appliances. Bond failures of orthodontic appliances represent a significant nuisance in terms of time and expense for both the practitioner and the patient that should be avoided if at all possible.

As a consequence, careful preparation of the appliances and the patient's teeth is an important task prior to the appliance bonding procedure. Preparation of the patient's teeth usually includes the steps of etching and priming the teeth following tooth cleaning. In one procedure, the practitioner applies an etchant such as phosphoric acid to each tooth using, for example, a small brush or swab. Next, the teeth are rinsed of the etchant and dried. The practitioner then applies a primer composition to each tooth, again using, for example, a small brush or swab. Alternatively, following tooth cleaning, the practitioner may choose to use a single composition that serves as both an etchant and a primer.

In any case, however, it is usually preferred to apply the etchant and primer compositions, or the combination etchant/primer composition, to only those areas of the teeth that will be adjacent the base of the appliance once the appliance has been bonded to the teeth. Etchant compositions are acidic and may irritate a patient's gingival tissue. For that reason, it is desired to carefully apply the etchant composition in a controlled manner with a small applicator so that contact with the gingival tissue is avoided.

Additionally, some patients may have an allergic reaction or develop a sensitivity to certain components present in orthodontic primers. Consequently, it is important to also carefully apply the primer to the patient's teeth in order to avoid contact of the primer with gingival tissue. It is also important to avoid placing primer in interproximal regions of the dental arch because the primer may hinder movement of the teeth to desired positions once the primer has hardened.

SUMMARY OF THE INVENTION

The present invention is directed toward methods and apparatus for applying an orthodontic composition to selected areas of multiple teeth simultaneously. The selected areas of the teeth that receive the composition substantially correspond to the areas of the teeth that will subsequently lie directly beneath the base of orthodontic appliances such as brackets and buccal tubes once the appliances are bonded to the teeth. The invention significantly reduces the amount of time needed for the practitioner to apply the composition to each of the patient's teeth.

Advantageously, the present invention helps insure that the application of excessive amounts of composition is avoided. As a consequence, the time and effort needed to clean excess composition from the tooth surface is reduced. Moreover, the present invention reduces the likelihood that the composition will come into contact with the patient's gingival tissue and other regions of the oral cavity to be avoided such as the interproximal regions of the dental arch.

In one embodiment, the apparatus includes wall portions having a configuration that matches the configuration of selected portions of the patient's dental arch. The composition is pre-applied to certain sections of the apparatus that correspond to intended areas of the patient's teeth that will ultimately receive the appliances. As the apparatus is placed on the patient's dental arch, the sections of the apparatus with the composition are automatically positioned adjacent the previously selected areas of the teeth and the composition is applied and transferred to all of the selected areas at the same time.

In more detail, the present invention is directed in one aspect to an apparatus for applying a composition to a patient's teeth for use in an orthodontic treatment program that includes a plurality of orthodontic appliances bonded to selected areas of the patient's teeth. The apparatus comprises a substrate having at least one wall portion with a configuration that matches the configuration of at least one portion of the patient's dental arch. The substrate also includes a plurality of transfer sections each corresponding to a respective tooth of the dental arch. The transfer sections are located adjacent the selected areas of the teeth to receive the appliances when the substrate is placed on the patient's dental arch. The apparatus also includes a quantity of composition applied to the transfer sections for transfer to the selected areas of the corresponding teeth when the substrate is placed on the patient's dental arch.

The present invention is directed in another aspect to a method of applying a composition to a patient's teeth. The method comprises:

providing a transfer apparatus having at least one wall portion with a configuration that matches the configuration of at least one portion of a patient's dental arch;

determining the locations of areas of a patient's teeth to receive orthodontic appliances;

determining the locations of sections of a transfer apparatus that correspond to the locations of the certain areas of the patient's teeth;

applying a quantity of composition to the sections of the transfer apparatus; and placing the transfer apparatus in contact with the dental arch in order to transfer at least part of the composition to the certain areas of the patient's teeth.

Another aspect of the present invention is directed to a method of making an apparatus for applying a composition to a patient's teeth. This method comprises:

providing a transfer apparatus having at least one wall portion with a configuration that matches the configuration of at least one portion of a patient's dental arch;

determining the locations of areas of the patient's teeth to receive orthodontic appliances;

determining the locations of sections of the transfer apparatus that correspond to the locations of the areas of the patient's teeth to receive orthodontic appliances; and applying a quantity of composition to the sections of the transfer apparatus.

Another aspect of the present invention is directed toward a method of bonding orthodontic appliances. This method comprises:

providing a transfer apparatus having at least one wall portion with a configuration that matches the configuration of at least one portion of a patient's dental arch;

applying a quantity of bonding composition to selected sections of the transfer apparatus;

placing the transfer apparatus in contact with the dental arch in order to transfer at least part of the bonding composition to certain areas of the patient's teeth;

removing the transfer apparatus from the dental arch; and subsequently bonding orthodontic appliances to the certain areas of the patient's teeth.

These and other features of the invention are described in the paragraphs that follow and are illustrated in the accompanying drawings.

DEFINITIONS

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Buccolabial" means in a direction toward the patient's lips or cheeks.

"Lingual" means in a direction toward the patient's tongue.

DETAILED DESCRIPTION OF THE PREFERRED EMBODIMENTS

Figure 1:
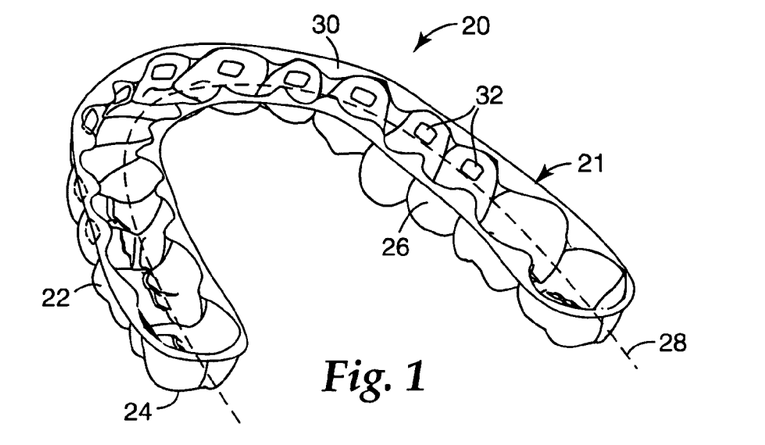
FIG. 1 is a perspective view of an orthodontic transfer apparatus for applying a composition to a patient's teeth according to one embodiment of the present invention.

A transfer apparatus for applying a composition to an orthodontic patient's teeth is broadly designated by the numeral 20 in FIG. 1. The apparatus 20 includes a substrate 21 having a buccolabial wall portion 22, a gingival wall portion 24 and a lingual wall portion 26. Preferably, the wall portions 22, 24, 26 are integrally connected to each other and form a unitary body.

The buccolabial wall portion 22, the occlusal wall portion 24 and the lingual portion 26 preferably have a configuration that matches the buccolabial portions, the occlusal portions and the lingual portions respectively of the patient's dental arch when the apparatus 20 is placed on the dental arch. Preferably, the configuration of the wall portions 22, 24, 26 is substantially identical to underlying portions of the patient's dental arch so that the apparatus 20 is matingly received on the dental arch in relatively tight-fitting relation. As a result, relative lateral movement between the dental arch and the apparatus 20 when the latter is placed on the dental arch is substantially avoided.

The apparatus 20 in the embodiments shown in FIG. 1 has a curved central longitudinal axis 28. The wall portions 22, 24, 26 present a generally "U"-shaped configuration in references planes perpendicular to the central axis 28. This "U"-shaped configuration defines a channel 30 that receives the dental arch.

The exemplary apparatus 20 that is shown in FIG. 1 has a shape adapted to extend along all of the teeth of one of the patient's dental arches. However, other constructions are also possible. For example, the apparatus 20 may have a length that extends along only some of the teeth of the dental arch. For instance, three transfer apparatus could be provided: one apparatus could have a configuration adapted to extend along the six teeth in the middle of the patient's dental arch, a second transfer apparatus could be adapted to extend along the bicuspid and molar teeth of the right hand side of the dental arch, and a third transfer apparatus could be adapted to extend along the bicuspid and molar teeth of the left hand side of the dental arch.

The transfer apparatus 20 includes a number of transfer sections 32. Preferably, a transfer section 32 is provided for each tooth that receives an adhesively bonded orthodontic appliance such as a bracket or a buccal tube. When the apparatus 20 is placed over the dental arch, each transfer section 32 is positioned directly over a certain pre-selected area of the tooth that is to receive the chosen orthodontic appliance.

As an option, each of the transfer sections 32 has a shape in reference planes perpendicular to a buccolabial-lingual reference axis that is similar in shape to the base of the respective orthodontic appliance. For example, if the orthodontic appliance has a base that is generally rectangular in shape, the transfer section 32 corresponding to that appliance will have a rectangular shape of similar configuration. Each of the transfer sections 32 has an overall area in reference planes perpendicular to a buccolabial-lingual reference axis that is preferably no greater than about 125% and more preferably no greater than about 110% of the overall area of the base of the selected, respective appliance.

Optionally, the transfer sections 32 are made of the same material as the substrate 21 and form an integral, unitary component. For example, the transfer sections 32 could be designated sections of a smooth interior surface of the buccolabial wall portion 22. As another example, the transfer sections 32 could be roughened regions, regions with pores or cavities, or regions formed with protrusions that are integral with remaining smooth regions of the interior surface of the buccolabial wall portion 22. As another option, the transfer sections 32 are made of a material that is different than the material of the substrate 21 and are adhered or otherwise fixed to the inner surface of the buccolabial wall portion 22.

Optionally, each of the transfer sections 32 provides a discrete reservoir in the channel 30 of the transfer apparatus 20 that is at least partially contained along its mesial, gingival, distal and occlusal sides. The provision of reservoirs with contained or partially contained sides increases the likelihood that the composition will be transferred only to the pre-selected areas of each tooth to receive an appliance, and not to adjacent areas including areas next to the gingival margin and interproximal areas between adjacent teeth.

In the embodiment shown in FIGS. 1 and 3–5, the transfer sections 32 include a plurality of protrusions 36 that are integrally connected to a backing 37. The backing 37 is fixed to the inner surface of the buccolabial wall portion 22. The protrusions 36 may be any one of a number of a variety of shapes, such as cones, truncated cones, rods, pyramids, truncated pyramids, cubes, gum drops, cylinders, nail heads or mushroom-shaped members, and the like. The protrusions 36 may have an outer end that is flat, rounded, pointed or another shape. In the illustrated embodiment, the protrusions 36 include a stem and an outer, enlarged head. The protrusions 36 are exaggerated in size in the drawings for the purposes of illustration, and preferably are much smaller and arranged in rows presenting a density ranging from, for example, 78 to 465 protrusions per square centimeter.

Optionally, the protrusions 36 may be made by a microreplication method such as the methods disclosed in U.S. Pat. No. 5,152,917 (Pieper et al.) and U.S. Pat. No. 5,500,273 (Holmes et al.). Various manufacturing processes for forming an array of upstanding added protrusions integral with a backing layer are described in U.S. Pat. No. 4,290,174 (Kalleberg), U.S. Pat. No. 4,984,339 (Provost et al.), WO 94/23610 (Miller et al.), WO 98/30381 (Miller et al.) and PCT/US97/15960 (Kempfer). An example of a suitable material for making the transfer sections 32 is a die-cut section of the hook side of a polypropylene micro-replicated mechanical fastener such as No. CS-200 diaper tape from 3M Company.

Other suitable materials for making the transfer sections 32 include non-woven materials and the materials described in U.S. Pat. Nos. 6,322,360, 6,142,780 and 6,126,443 (Burgio).

The apparatus 20 further includes a composition 34 that is received on each of the transfer sections 32. The composition 34 preferably extends across a substantial majority of the area of each transfer section 32, and more preferably extends across the entire area of each transfer section 32. Such construction helps ensure that the composition 34 is transferred to at least a majority, if not entirely all, of the selected area of the respective tooth to receive the base of the appliance.

The composition 34 may comprise one or more of the following: an etchant, an adhesive primer, an adhesive, an adhesive component and a sealant. Suitable examples of the composition 34 include "TRANSBOND" XT brand etchant gel, "TRANSBOND" XT brand primer, and "TRANSBOND" MIP primer, all from 3M Unitek Corporation. The composition 34 may also comprise methacrylated phosphoric esters such as those found in self-etching orthodontic primers including "TRANSBOND" PLUS brand self-etching primer, from 3M Unitek Corporation. The composition 34 may also comprise a self-etching orthodontic adhesive or a self-adhesive composition. A suitable sealant is "CLINPRO" brand sealant from 3M Espe. As another alternative, the composition 34 may comprise a liquid that later serves to activate an ionic cement that has been precoated onto the base of an orthodontic appliance such as described in U.S. Pat. No. 6,050,815 (Adam et al.).

As another option, the composition 34 may be a color-changing composition. For example, the composition 34 may change in color upon exposure to actinic radiation, upon contact with other compositions or after a period of time. Examples of color-changing orthodontic adhesives are described in U.S. Pat. No. 6,528,555. The composition 34 may be a color-changing primer having an initial color that contrasts with the color of the tooth and a final color that is clear or closely matches the color of the tooth. The use of a color-changing primer composition is an advantage when the apparatus 20 is used prior to a direct bonding procedure, since the initial color of the primer can provide a "target" for properly placing and positioning the appliance on the tooth. The initial color of the primer composition also facilitates clean-up of excess composition subsequent to placement of the appliance. After the primer has changed color, it is rendered aesthetic and is difficult to see.

As an alternative to the constructions set out above, one or more of the transfer sections 32 may be constructed to omit the application of composition to certain areas of the tooth that will lie beneath the appliance base. For example, a transfer section 32 may have an overall width in a mesial-distal direction that is less than the overall width of the appliance base. When the transfer section 32 is used to apply a bonding composition to the tooth, the composition is omitted in portions of the apparatus 20 corresponding to areas of the tooth that will subsequently lie beneath mesial and distal edge portions of the appliance, thereby reducing the bond strength between the appliance and the tooth in those areas. The adhesive bond in remaining areas beneath the appliance base is sufficient to securely retain the appliance on the tooth during the normal course of treatment, but the appliance can be readily debonded when desired by pivoting the appliance about an occlusal-gingival reference axis.

As another example, the transfer section 32 may have an overall height in an occlusal-gingival direction that is less than the overall height of the appliance base. The transfer section 32 applies bonding composition to areas that will subsequently lie beneath the appliance base except for a gingival edge portion of the base. In this example, the adhesive bond in remaining areas of the appliance is sufficient to securely retain the appliance on the tooth during the course of treatment, but the appliance can be readily debonded from the tooth when desired by pivoting the appliance about a mesial-distal reference axis.

Figure 2:
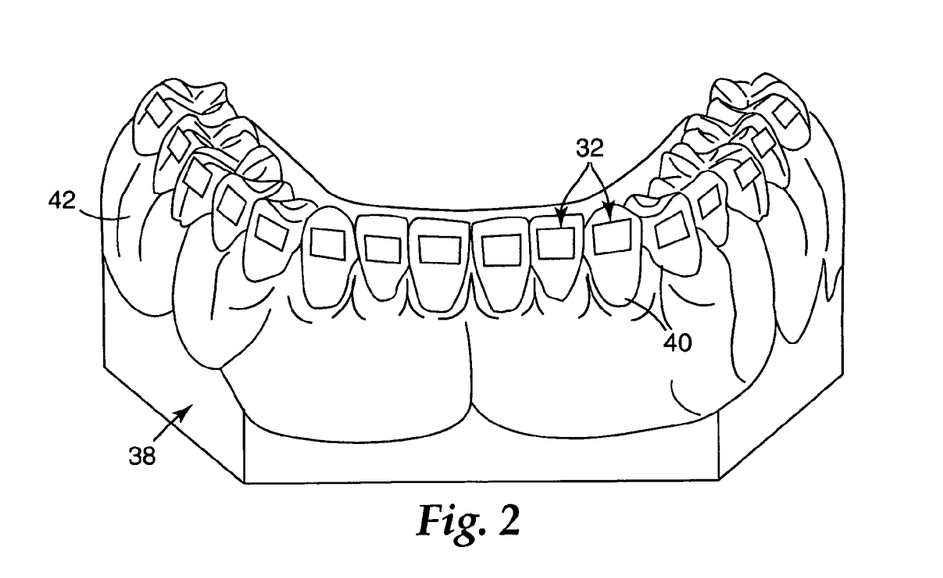
FIG. 2 is a front elevational view of an exemplary model of a patient's dental arch for use in making the transfer apparatus shown in FIG. 1, and illustrating a plurality of appliqués connected to selected areas of the teeth of the model dental arch to serve as transfer sections.

A preferred method of making the transfer apparatus 20 includes the act of making a model of the patient's dental arch. FIG. 2 illustrates a model 38 of an exemplary lower dental arch of an orthodontic patient. Alternatively, the model dental arch may be a replica of the patient's upper dental arch. As a further option, the model may represent only a portion of the upper or lower dental arch, such as the anterior and cuspid teeth of the arch. In the example illustrated, the model 38 includes a number of model teeth 40 representing all of the teeth of the lower dental arch.

Optionally, the model arch 38 is made by first taking an impression of the patient's lower dental arch, using care to avoid undue distortion. Optionally, an alginate impression material is used such as Unijel II brand alginate impression material from 3M Unitek Corporation. Alternatively, a hydrocolloid or vinyl polysiloxane impression material may also be used, such as Position Penta brand vinyl polysiloxane impression material from 3M ESPE.

The model arch 38 is then made from the impression. Optionally, the model arch 38 is a "stone" model made from plaster of Paris, using care to avoid bubbles in the model. If small voids are present, the voids can be filled with a small, additional quantity of plaster of Paris. As an option, the model arch 38 includes only the model teeth 40 and sufficient replica gingival tissue 42 to hold the model teeth 40 together.

As an alternative, the model arch 38 may be made using digital data that is representative of the patient's teeth and adjacent gingival tissue. The digital data may be obtained by use of a hand-held intra-oral scanner or other device known in the art. As another option, the digital data may be obtained by scanning an impression or a stone model made from an impression. The model arch 38 may then be made from the digital data using, for example, a stereolithographic printer or a CNC milling machine similar to the CAD/CIM milling machines sold by Cerec Network of Buelach, Switzerland. The intra-oral camera associated with the Cerec machines may be used to obtain digital data mentioned above.

Preferably, the model arch 38 is an accurate replica of the patient's oral structure. In particular, the model teeth 40 preferably have a size, shape and orientation that is identical to the size, shape and orientation of the corresponding teeth of the orthodontic patient.

Figure 3:
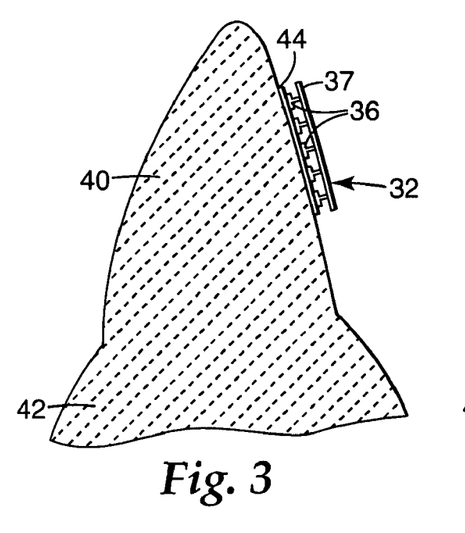
FIG. 3 is an enlarged side cross-sectional view of one of the model teeth and appliqués illustrated in FIG. 2.

Next, and as shown in FIG. 3, a transfer section 32 is applied to each model tooth 40 that is to receive an orthodontic appliance. Preferably, however, before the transfer section 32 is applied to the model tooth 40, a determination is first made of the exact location of the orthodontic appliance on the respective tooth of the patient. The corresponding location of this selected area is then found on the model tooth 40.

For example, the practitioner may use hand instruments such as gauges to determine the location of the bracket base with respect to the model tooth. For instance, if the archwire slot of the selected bracket is to be 5 mm from the incisal edge of the patient's tooth, a 5 mm gauge may be used to assist in drawing a pencil line on the model tooth that is 5 mm from its incisal edge. The practitioner may then mark the intersection of the long axis of the model tooth with the drawn pencil line, using a visual assessment of the shape of the model tooth to determine the location of the long axis.

As another option, the practitioner may choose to use computer software to determine the proper placement of the selected appliance and hence the proper placement of the transfer section. For example, the practitioner may desire the appliance to be aligned with the facial axis point of the clinical crown (the "FA point") of the tooth, such that the archwire slot of the bracket is oriented in a plane parallel to the patient's occlusal plane and the occlusal-gingival axis of the bracket is aligned with the long axis of the patient's tooth. The software utilizes a digital data file representative of the patient's tooth and determines the location of the FA point. The FA point on the model tooth 40, corresponding to the same FA point on the patient's tooth, is then located. In addition, the orientation of the archwire slot and the occlusal-gingival axis of the bracket are then determined with respect to the model tooth 40, using the FA point of the model tooth 40, a determination of the occlusal plane of the dental arch and a determination of the long axis of the tooth. A suitable computer program for determining the long axis of a tooth is described in U.S. Patent Publication no. 2004/0054304 (Raby). Subsequently, the area that the bracket base will cover on the patient's tooth (and which will correspond to the area covered by the transfer section 32 on the model tooth 40) is determined, using known information regarding the dimensions of the base of the selected bracket.

Next, the transfer section 32 is prepared by trimming stock material as needed until the dimensions of the transfer section 32 are similar to the dimensions of the selected bracket base. The transfer section 32 is then applied to the model tooth 40 as illustrated in FIG. 3 in such a manner that the transfer section 32 is placed in the selected area of the model tooth 40 that corresponds to the selected area of the patient's tooth that will ultimately receive the base of the bracket. For instance, and with respect to the example set out above, the transfer section 32 may be manipulated as needed until, for example, the center of the transfer section 32 lies over the FA point, the mesial and distal edges are parallel with the selected orientation of the occlusal-gingival reference axis of the bracket and the occlusal and gingival edges are parallel with the selected orientation of the archwire slot of the bracket.

As an alternative to determining the exact location of the orthodontic appliance as described above, the practitioner may elect to instead determine only an approximate location of the appliance. For example, the practitioner may elect to apply the composition 34 (such as, for example, a primer or etchant) to the entire facial or buccolabial surface of the tooth crown, except for a 3 mm boundary or peripheral edge region that extends along the gingival margin, the interproximal regions and the occlusal edge of the tooth. In this manner, the appliance may be placed anywhere within the boundary and optionally manipulated later as desired to a precise location and orientation. In this alternative procedure, the transfer sections 32 may be prepared ahead of time by trimming the sections 32 to the approximate shapes of the buccolabial surfaces of the teeth, minus the boundary regions.

The transfer sections 32 may be applied to the teeth of the model arch 38 by hand. Alternatively, a robotic arm may be used to pick up the transfer sections 32 and apply the same to the model arch 38, using the digital data described above.

Once all of the transfer sections 32 have been applied to respective model teeth 40 as may be desired, a sheet of polymeric material such as the thermoplastic materials mentioned above is placed over the model arch 38 including the transfer sections 32. The sheet of material is then thermoformed or vacuumed formed over the model arch 38 and the transfer sections 32 in order to conform the sheet of material to the configuration of the model arch 38. Heat may be applied during the forming process in order to facilitate conformance of the sheet of material to the exact configuration of the model arch 38 and transfer sections 32. The formed apparatus 20 is illustrated in FIG. 4.

Figure 4:
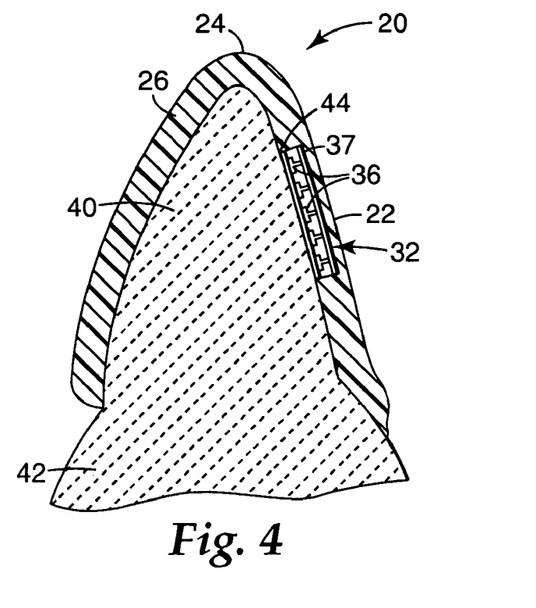
FIG. 4 is an enlarged side cross-sectional view of a sheet of polymeric material being formed over the model tooth and appliquédepicted in FIG. 3 in order to make the transfer apparatus shown in FIG. 1.

In the embodiment shown in FIGS. 3 and 4, the transfer sections 32 are appliqués that initially include an adhesive sheet 44 having a layer of adhesive on both sides. The adhesive sheet 44 retains the transfer sections 32 in place on the model teeth 40 during the forming of the sheet of material to make the apparatus 20. Once the apparatus 20 has been formed and cooled, the apparatus 20 is removed from the model arch 38 and the adhesive sheet 44 is detached from the transfer sections 32 and discarded.

In the illustrated embodiment, the transfer sections 32 are embedded within the sheet of material forming the wall portions 22, 24, 26. Alternatively, or in addition, an adhesive may be provided to securely fix the transfer sections 32 to the wall portion 22.

Once the apparatus 20 has been detached from the model arch 38, the apparatus 20 is trimmed as desired. Preferably, the trimming operation includes trimming of the lingual wall portion 26 so that, for example, it extends only about one-half of the distance from the occlusal edge of the tooth to the lingual margin of the exposed tooth crown. The buccolabial wall portion 22 is also trimmed to avoid contact with the gingival tissue.

Next, and after the adhesive sheet 44 has been detached from the protrusions 36, the composition 34 (FIG. 5) is applied to each of the transfer sections 32. Optionally, the composition 34 may be dispensed onto the transfer sections 32 in automated fashion, using a robotic arm that is connected to a source of the composition 34. For example, the end of the robotic arm may carry a cannula having a solenoid valve, and the cannula is coupled by tubing to a pressurized container of the composition 34. The apparatus 20 is placed on a support and the robotic arm dispenses composition through the cannula to each of the transfer sections 32 in sequential fashion. Movement of the robotic arm and dispensing of the composition by operation of the valve are controlled by a computer, using the digital data that represents the dimensions and location of each transfer section 32.

When the practitioner elects to bond appliances to the patient's teeth, the patient's teeth are cleaned and rinsed in preparation to receive the composition 34. If the composition 34 is a primer that should be applied to dry teeth, the patient's teeth are then dried using a stream of air. The transfer apparatus 20 is then placed over the corresponding dental arch of the patient and seated, optionally with a swinging, hinge-type motion. Since the shape of the channel 30 matches the shape of the underlying dental arch, the transfer sections 32 are simultaneously seated against the areas of the patient's teeth at precisely the same locations corresponding to the previous position of the transfer sections 32 on the model teeth 40.

Figure 5:
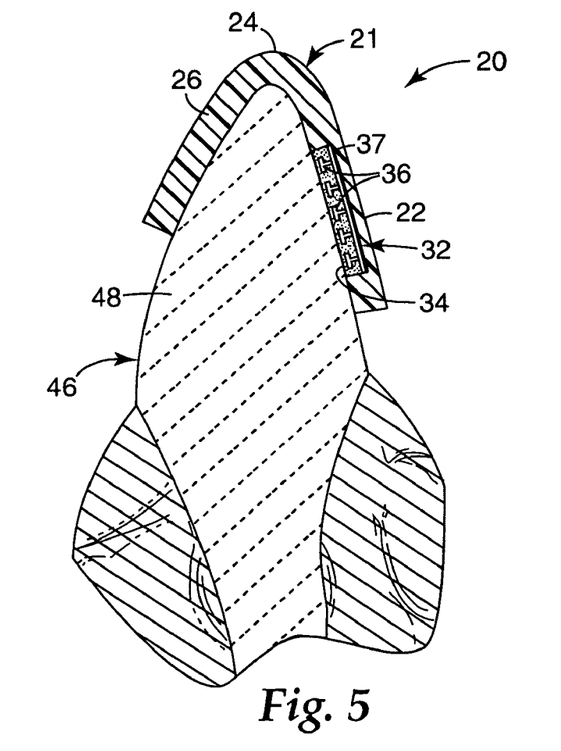
FIG. 5 is an enlarged side cross-sectional view of the transfer apparatus illustrated in FIG. 4 after the apparatus has been removed from the model teeth, trimmed and placed in contact with the patient's teeth.

FIG. 5 is an illustration showing the transfer apparatus 20 in place over a dental arch 46 of an orthodontic patient. Once the apparatus 20 is in place, each of the transfer sections 32 extends over and is preferably in contact with a corresponding tooth 48 of the dental arch 46. The composition 34 associated with each transfer section 32 then wets the adjacent areas of the tooth 48 and partially transfers to the same. Preferably, light finger pressure is then applied to the buccolabial wall portion 22 in areas over each of the transfer sections 32 to help ensure that a sufficient amount of the composition 34 has been transferred to the selected areas of the patient's tooth enamel.

After the composition 34 has been transferred to the selected areas of the patient's teeth, the transfer apparatus 20 is detached from the dental arch 46 and removed from the patient's oral cavity. Depending upon the choice of the composition 34, the composition 34 is then dried as needed. Subsequently, an orthodontic appliance such as a bracket or buccal tube is bonded to the area of the patient's tooth 48 that has received the composition 34. The appliances may be placed on the selected areas of the patient's teeth by hand, using hand instruments or bracket placement instruments having a built-in gauge. Alternatively, each of the appliances is oriented using the digital data described above in order to align its archwire slot and occlusal-gingival reference axis with the orientations of the archwire slot and occlusal-gingival reference axis selected earlier.

Figures 6, 7:
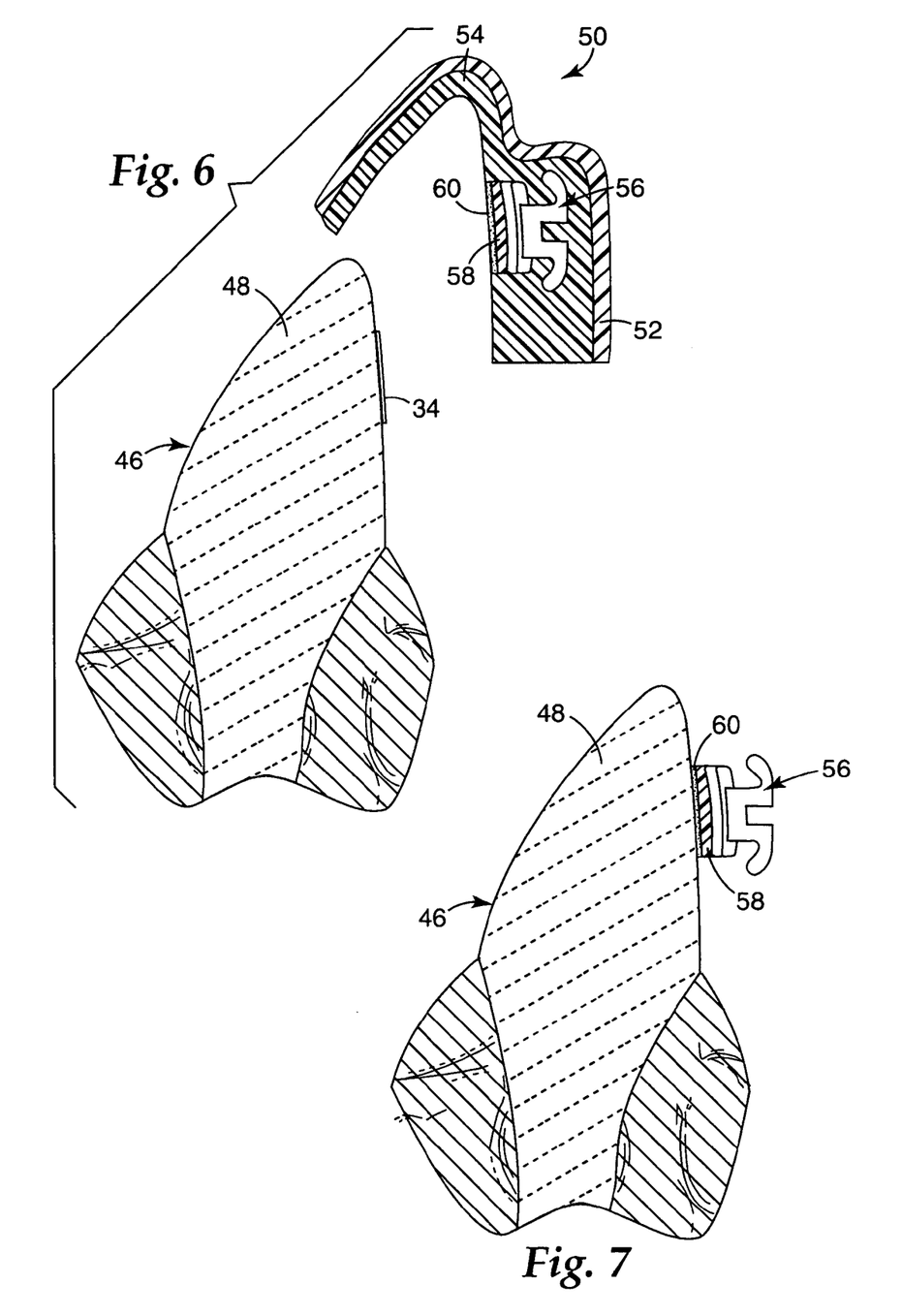
FIG. 6 is a view somewhat similar to FIG. 5 except that the transfer apparatus has been removed from the patient's teeth, and wherein also is shown an exemplary indirect bonding tray for bonding orthodontic appliances to the patient's teeth.
FIG. 7 is a view somewhat similar to FIG. 6 except that the appliance has been bonded to the patient's tooth and the indirect bonding tray has been removed.

FIG. 6 is an illustration of an exemplary bonding technique using an indirect bonding tray 50. In this example, the bonding tray 50 includes a shell 52 and matrix material 54. The transfer tray 50 also includes a plurality of appliances 56 (only one is shown) that, in this example, is an orthodontic bracket. The appliances 56 are positioned in the tray 50 using the digital data described above. The appliances 56 preferably include a custom base 58 and a quantity of orthodontic adhesive 60. Suitable appliances include appliances that are precoated with a light-curable adhesive such APC brand adhesive precoated appliances from 3M Unitek Corporation. Alternatively, an adhesive (chemical-cure or photocurable) may be applied to the appliances by hand.

The tray 50 is applied to the dental arch 46 in a manner similar to the application of the apparatus 20. In particular, the tray 50 is positioned over the corresponding teeth and seated, optionally using a swinging, hinge-type motion. The shape of the cavity presented by the matrix material 54 matches the shape of the patient's underlying teeth, and as a result the appliances 56 are simultaneously seated against the teeth at locations that correspond to previously selected locations. Preferably, pressure is applied to the occlusal, labial and buccolabial surfaces of the shell 52 until such time as the adhesive 60 has sufficiently hardened. Optionally, finger pressure may be used to firmly press the appliances 56 against the enamel surfaces of the patient's teeth.

Once the adhesive 60 is hardened, the tray 50 is carefully removed from the patient's dental arch 46. Preferably, the shell 52 is first separated from the matrix material 54, which remains in place over the dental arch 46 along with the appliances 56. Next, the matrix material 54 is detached from the appliances 56. Optionally, a hand instrument such as a scaler may be used to help hold each appliance 56 in place against the surface of the respective tooth 48 of the patient as the matrix material 54 is peeled away from the appliances 56.

Preferably, the transfer tray 50 is made according to the disclosure of applicant's pending U.S. patent application entitled "APPARATUS FOR INDIRECT BONDING OF ORTHODONTIC APPLIANCES AND METHOD OF MAKING THE SAME"; U.S. Ser. No. 10/678,286 filed Oct. 3, 2003. Other aspects and additional options for the transfer tray 50 are set out in that patent application. Preferably, a duplicate model arch that is identical to the model arch 38 is used to make the tray 50. As another option, the model arch 38 used to make the transfer apparatus 20 may be also used to make the tray 50. The digital data used to determine the orientation and location of the transfer sections 32 is also used to determine the location and orientation of the appliances 56.

FIG. 7 is an illustration depicting one of the appliances 56 mounted on one of the patient's teeth 48, showing the appliance 56 held securely in place by the bond to the patient's tooth enamel provided by the hardened adhesive 60. The appliance 56 is now ready to receive an archwire in order to initiate orthodontic treatment.

Figure 8:
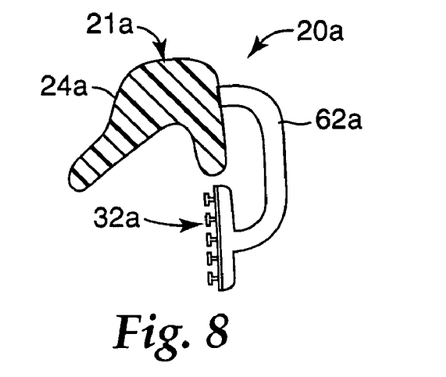
FIG. 8 is a side cross-sectional view of an orthodontic transfer apparatus for applying a composition to a patient's teeth according to another embodiment of the invention.

A transfer apparatus 20a according to another embodiment of the invention is shown in cross-sectional view in FIG. 8. Except as described below, the transfer apparatus 20a is substantially the same as the transfer apparatus 20 set out above.

The transfer apparatus 20a includes a substrate 21a in the form of a jig. The substrate 21a includes an occlusal wall portion 24a adapted to fit over an occlusal portion of the patient's dental arch. Preferably, the substrate 21a has a cavity with a configuration that is substantially identical to the occlusal portion of the patient's dental arch so that the apparatus 20a is matingly received on the dental arch in relatively tight-fitting relation.

The transfer apparatus 20a also includes a number of arms 62a connected to the substrate 21a. Optionally, an arm 62a is provided for each tooth corresponding to the number of teeth to receive the composition. A transfer section 32a is connected to each arm 62a and is oriented to apply the composition to pre-selected areas of the dental arch.

Preferably, the transfer sections 32a are identical to the transfer sections 32 described above. The transfer sections 32a may be coupled to the arms 62a by an adhesive, although other options are also possible. Following application of the composition to the patient's tooth surfaces, the transfer apparatus 20a is removed from the dental arch. Orthodontic appliances are then bonded to the areas of the teeth that have received composition transferred by the transfer sections 32a.

Figure 9:
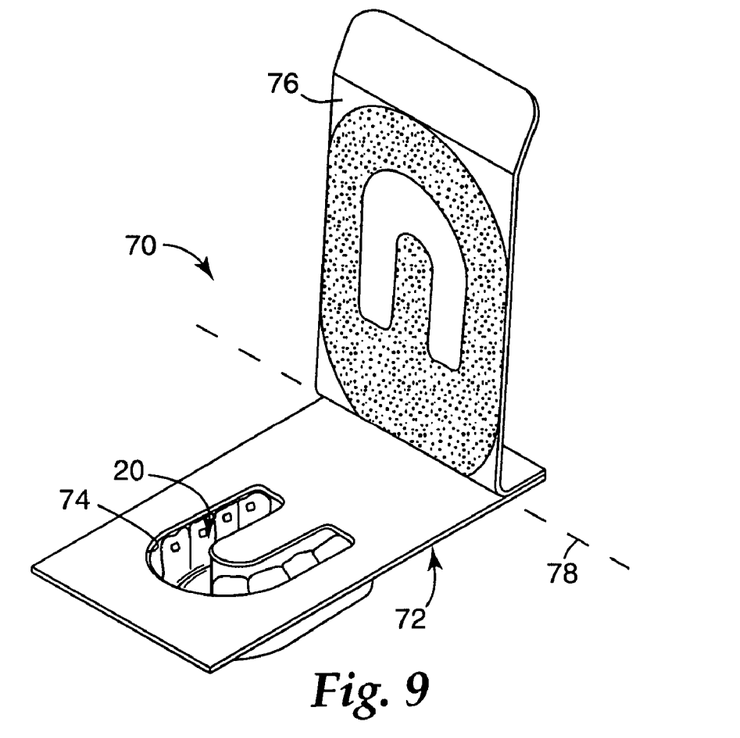
FIG. 9 is a perspective view showing a packaged article that includes a container and a transfer apparatus received in a chamber of the container according to yet another embodiment of the invention.
Figure 10:
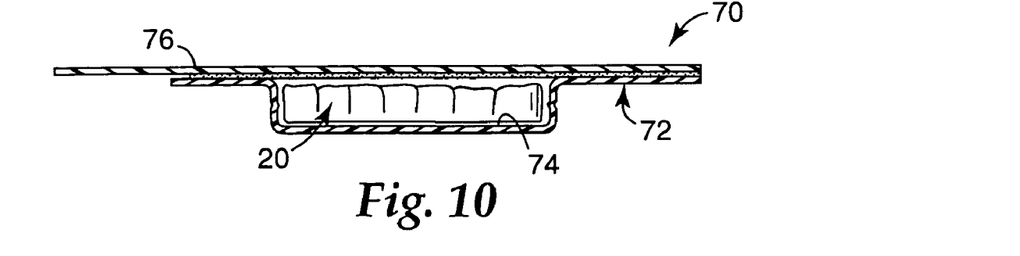
FIG. 10 is a side cross-sectional view of the packaged article shown in FIG. 9, except that a cover of the container has been closed.

Optionally, the transfer apparatus of the present invention can be provided as part of a packaged article that is ready for use. In FIGS. 9 and 10, a packaged article 70 is shown and includes the transfer apparatus 20 described above for purposes of illustration. However, transfer apparatus constructed in accordance with other embodiments of the invention, such as the transfer apparatus 20a, may be used in place of the apparatus 20.

The packaged article 70 includes a container 72 having a chamber 74. A cover 76 of the container 72 is movable between a closed position as shown in FIG. 10 wherein the cover 76 extends across the chamber 74 and an open position as shown in FIG. 9 wherein the cover 76 is spaced apart from the chamber 74 for access to the transfer apparatus 20.

In the embodiment shown in FIGS. 9 and 10, the container 72 has a generally "U"-shaped bottom and an upright side wall that defines a generally "U"-shaped configuration in bottom view. A rectangular top flange surrounds an opening to the chamber 74 and is integrally connected to the side wall of the container 72. A pressure sensitive adhesive on the cover 76 engages the top flange for releasably retaining the cover 76 in the closed position. Other constructions are also possible.

Preferably, the chamber 74 has structure that contacts the transfer apparatus 20 so that the latter does not unduly shift when the cover 76 is closed. For example, the sides of the chamber 74 may have a shape complemental to the shape of the transfer apparatus 20. Alternatively, bars, posts or other structure could be provided in the chamber 74 to contact the transfer apparatus 20 and prevent undue movement.

As an additional option, the chamber 74 may have structure for facilitating gripping of the sides of the transfer apparatus 20 so that the apparatus 20 can be easily removed from the chamber 74 when desired. For example, sides of the chamber 74 may have recesses for receiving the practitioner's fingers, so that the sides of the transfer apparatus 20 can be easily grasped. As another option, the posts or bars mentioned in the previous paragraph could be properly sized and spaced apart from each other in order to enhance gripping of the sides of the transfer apparatus 20.

The cover 76 is constructed to protect the composition 34 from contaminates such as dust, moisture and the like. In addition, when the composition 34 is an adhesive, primer or etchant, the container 72 including the cover 76 is constructed to avoid deterioration of the bonding characteristics provided by the composition 34, so that the ultimate strength of the bond between the appliance and tooth is relatively high. If, for example, the composition 34 is curable upon exposure to actinic radiation, the container 72 is constructed of a material that provides a substantial barrier to the transmission of actinic radiation. Suitable materials for the container 72 include flexible plastic materials such as black or red polyethyleneterephthalate glycol (PETG). Preferably, the container 72 is made of a material that substantially hinders the passage of actinic radiation but enables the passage of light in at least a portion of the visible spectrum so that the presence of the transfer apparatus 20 within the container 72 can be confirmed without opening the cover 76. As another option, the cover 76 may include a layer of paper that is bonded to a barrier layer such as aluminum foil. Examples of suitable materials for the container 72 as well as methods for constructing the container 72 are set out in applicant's U.S. Pat. Nos. 5,538,129 and 5,354,199 as well as in applicant's pending U.S. patent application entitled "CONTAINERS FOR PHOTOCURABLE MATERIALS" Ser. No. 10/126804, filed Apr. 18, 2002.

Alternatively, the container 72 may include a hermetic seal in regions between the flange of the container 72 and the cover 76 instead of the pressure sensitive adhesive. The use of a hermetic seal helps to prevent volatile components of the composition 34 from contacting a pressure sensitive adhesive such as the pressure sensitive adhesive on the cover 76 as described above. As a result, the hermetic seal decreases the loss of volatile components from within the chamber 74.

As an additional option, the container 72 may be provided with an additional quantity of one or more components of the composition 34 that are volatile, in order to help decrease the loss of volatile components that are present in the composition 34. For example, the composition 34 may be an adhesive that contains ethyl 4-dimethylaminobenzoate ("EDMAB") and/or camphorquinone ("CPQ"), both of which may volatilize over a period of time after the container 72 is closed. By adding an additional quantity of such components in the chamber 74, equilibrium is shifted and there is less likelihood of losing an undue quantity of such components from the composition 34 that is applied to the apparatus 20. As a result, there is less likelihood that the characteristics of the composition 34 are impaired over a period of time. The additional volatile components may be provided in a liquid that is placed in a well adjoining the chamber 74, or may be placed in a porous material (such as a sponge or fabric) that optionally serves as a packing material for the transfer apparatus 20.

Preferably, the container 72 is constructed so that the cover 76 is self-retained in the open position as illustrated in FIG. 9 once the container 72 is opened. To this end, the cover 76 may be provided with a line of weakness such as a series of perforations that extends along an axis that is designated 78 in FIG. 9. In addition to helping retain the cover 76 in an open orientation, the perforations also provide tactile feedback to the user that the cover 76 is open so that the user does not continue to pull on the cover 76 and separate the same from the flange of the container 72.

All of the patent and patent applications identified herein are expressly incorporated by reference. Additionally, those skilled in the art will recognize that many modifications and alternative constructions may be made without departing from the essence of this invention. Accordingly, the invention should not deemed limited to the specific examples described in detail above, but instead only by a fair scope of the claims that follow along with their equivalents.

The invention claimed is:

1. A combination comprising
apparatus for applying a composition to a patient's teeth for use in an orthodontic treatment program that includes a plurality of orthodontic appliances bonded to selected areas of the patient's teeth, the apparatus comprising:
a substrate having at least one wall portion with a configuration that matches the configuration of at least one portion of the patient's dental arch, the substrate also including a plurality of transfer sections each corresponding to a respective tooth of the dental arch, and wherein the transfer sections are located adjacent the selected areas of the teeth to receive the appliances when the substrate is placed on the patient's dental arch; and
a quantity of a composition applied to the transfer section for transfer to the selected areas of the corresponding teeth when the substrate is placed on the patient's dental arch; and
an indirect bonding tray that includes a plurality of orthodontic appliances, the appliances being positioned in the tray to seat against the teeth at the selected areas of the teeth.

2. The combination of claim 1 wherein the substrate comprises a formed sheet of thermoplastic material.

3. The combination of claim 2 wherein the thermoplastic material comprises ethylene vinyl acetate.

4. The combination of claim 2 wherein the substrate includes a buccolabial wall portion and an occlusal wall portion.

5. The combination of claim 4 wherein the substrate further includes a lingual wall portion.

6. The combination of claim 1 wherein the transfer sections comprise a plurality of protrusions.

7. The combination of claim 1 wherein the composition comprises one or more of the following: an etchant, an adhesive primer, an adhesive, an adhesive component, and a sealant.

8. The combination of claim 1 wherein the transfer sections are bonded to the substrate.

9. The combination of claim 1 wherein the transfer sections each have a shape that generally matches the shape of the respective orthodontic appliance.

10. A packaged article comprising a container including a chamber, and where the apparatus of claim 1 is received in the chamber.

11. The packaged article of claim 10 wherein the composition comprises one or more of the following: an etchant, an adhesive primer, an adhesive, an adhesive component, and a sealant.

12. The packaged article of claim 10 wherein the chamber has a configuration substantially matching the configuration of the apparatus device.

13. A method of applying a composition to a patient's teeth comprising:
providing a transfer apparatus having at least one wall portion with a configuration that matches the configuration of at least one portion of a patient's dental arch;
determining the locations of certain areas of the patient's teeth to receive orthodontic appliances;
determining the locations of sections of the transfer apparatus that correspond to the locations of the certain areas of the patient's teeth;
applying a quantity of composition to the sections of the transfer apparatus, wherein the act of applying a quantity of composition includes the act of activating a robotic arm that is connected to a source of the composition in order to apply the composition to the sections of the transfer apparatus; and
placing the transfer apparatus in contact with the dental arch in order to transfer at least part of the composition to the certain areas of the patient's teeth.

14. The method of applying a composition to a patient's teeth according to claim 13 wherein the act of providing a transfer apparatus includes the act of making a model of at least a portion of a patient's dental arch and the act of forming a material over the model.

15. The method of applying a composition to a patient's teeth according to claim 13 wherein the composition includes one or more of the following: an etchant, an adhesive primer, an adhesive, an adhesive component, and a sealant.

16. The method of applying a composition to a patient's teeth according to claim 13 wherein the sections of the transfer apparatus each have an overall area that is no greater than about 125% of the selected, respective areas of the patient's teeth.

17. The method of applying a composition to a patient's teeth according to claim 13 wherein at least one of the act of providing a transfer apparatus, the act of determining the locations of the certain areas of the patient's teeth to receive orthodontic appliances, and the act of determining the locations of the sections of the transfer apparatus is carried out using digital data.

18. A method of applying a composition to a patient's teeth comprising:
providing a transfer apparatus having at least one wall portion with a configuration that matches the configuration of at least one portion of a patient's dental arch;
determining the locations of certain areas of the patient's teeth to receive orthodontic appliances;
determining the locations of sections of the transfer apparatus that correspond to the locations of the certain areas of the patient's teeth;
applying a quantity of composition to the sections of the transfer apparatus; and
placing the transfer apparatus in contact with the dental arch in order to transfer at least part of the composition to the certain areas of the patient's teeth, wherein the act of providing a transfer apparatus includes the act of placing appliqués over areas of the model that correspond to the certain areas of the patient's teeth.

19. The method of applying a composition to a patient's teeth according to claim 18 wherein each appliqué includes a number of protrusions.

20. A method of making an apparatus for applying a composition to a patient's teeth comprising:
providing a transfer apparatus having at least one wall portion with a configuration that matches the configuration of at least one portion of a patient's dental arch;
determining the locations of areas of the patient's teeth to receive orthodontic appliances;
determining the locations of sections of the transfer apparatus that correspond to the locations of the areas of the patient's teeth to receive orthodontic appliances; and
applying a quantity of composition to the sections of the transfer apparatus, wherein the act of providing a transfer apparatus includes the act of placing appliqués over areas of the model that correspond to the certain areas of the patient's teeth.

21. The method of making apparatus for applying a composition to a patient's teeth according to claim 20 wherein the act of providing a transfer apparatus includes the act of making a model of at least a portion of a patient's dental arch and the act of forming a material to conform to at least a portion of the model.

22. The method of making apparatus for applying a composition to a patient's teeth according to claim 20 wherein the composition includes one or more of the following: an etchant, an adhesive primer, an adhesive, an adhesive component, and a sealant.

23. The method of making apparatus for applying a composition to a patient's teeth according to claim 20 wherein the sections of the transfer apparatus each have an overall area that is no greater than about 125% of the selected, respective areas of the patient's teeth.

24. The method of making apparatus for applying a composition to a patient's teeth according to claim 20 wherein at least one of the act of providing a transfer apparatus, the act of determining the locations of the certain areas of the patient's teeth to receive orthodontic appliances, and the act of determining the locations of the sections of the transfer apparatus is carried out using digital data.

25. The method of making apparatus for applying a composition to a patient's teeth according to claim 20 wherein the act of providing a transfer apparatus includes the act of placing the transfer apparatus in a container, and wherein the act of applying a quantity of bonding composition is carried out before the act of placing the transfer apparatus in a container.

26. A method of making an apparatus for applying a composition to a patient's teeth comprising:
providing a transfer apparatus having at least one wall portion with a configuration that matches the configuration of at least one portion of a patient's dental arch;
determining the locations of areas of the patient's teeth to receive orthodontic appliances;
determining the locations of sections of the transfer apparatus that correspond to the locations of the areas of the patient's teeth to receive orthodontic appliances; and
applying a quantity of composition to the sections of the transfer apparatus,
wherein the act of applying a quantity of composition includes the act of activating a robotic arm that is connected to a source of the composition in order to apply the composition to the sections of the transfer apparatus.

27. A method of bonding orthodontic appliances comprising:
providing a transfer apparatus having at least one wall portion with a configuration that matches the configuration of at least one portion of a patient's dental arch;
applying a quantity of bonding composition to selected sections of the transfer apparatus;
placing the transfer apparatus in contact with the dental arch in order to transfer at least part of the bonding composition to certain areas of the patient's teeth;
removing the transfer apparatus from the dental arch; and subsequently
bonding orthodontic appliances to the certain areas of the patient's teeth.

28. The method of bonding orthodontic appliances according to claim 27 and including the act of providing a model of the patient's dental arch, and wherein the act of providing a transfer apparatus includes the act of forming a sheet of thermoplastic material over the model.

29. The method of bonding orthodontic appliances according to claim 28 and including the act of applying a plurality of appliqués to the model in locations corresponding to the certain areas of the patient's teeth.

30. The method of bonding orthodontic appliances according to claim 29 wherein the selected sections comprise the appliqués.

31. The method of bonding orthodontic appliances according to claim 27 wherein the act of applying a quantity of bonding composition to selected sections of the transfer apparatus is carried out at least in part using digital data.

32. The method of bonding orthodontic appliances to teeth according to claim 27 wherein the act of bonding orthodontic appliances to the certain areas of the patient's teeth is carried out with an indirect bonding placement apparatus.

33. The method of bonding orthodontic appliances to teeth according to claim 27 wherein the act of providing a transfer apparatus includes the act of placing the transfer apparatus in a container, and wherein the act of applying a quantity of bonding composition is carried out before the act of placing the transfer apparatus in a container.

34. The method of bonding orthodontic appliances to teeth according to claim 27 wherein the act of applying a quantity of bonding composition to selected sections of the transfer apparatus includes the act of omitting bonding composition in portions of the transfer apparatus that correspond to portions of the teeth that will subsequently underlie edge portions of the appliance.

* * * * *